United States Patent
Greenberg et al.

(10) Patent No.: US 8,934,983 B2
(45) Date of Patent: *Jan. 13, 2015

(54) FIELD FOCUSING AND MAPPING IN A VISUAL PROSTHESIS

(71) Applicant: Second Sight Medical Products, Inc., San Fernando, CA (US)

(72) Inventors: Robert J Greenberg, Los Angeles, CA (US); Richard Williamson, Santa Monica, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/649,011

(22) Filed: Oct. 10, 2012

(65) Prior Publication Data
US 2013/0035743 A1    Feb. 7, 2013

Related U.S. Application Data

(62) Division of application No. 12/487,498, filed on Jun. 18, 2009, now Pat. No. 8,311,635, which is a division of application No. 10/355,793, filed on Jan. 31, 2003, now Pat. No. 7,565,202.

(51) Int. Cl.
*A61F 9/08* (2006.01)
*A61N 1/36* (2006.01)

(52) U.S. Cl.
CPC .............. *A61F 9/08* (2013.01); *A61N 1/36185* (2013.01)
USPC ................. 607/54; 607/53; 607/67; 607/115; 607/116; 607/118; 607/139; 607/141

(58) Field of Classification Search
USPC ............... 607/1–2, 53–57, 67, 115–116, 118, 607/139, 141; 623/6.11, 6.22, 6.23; 351/49, 351/160 R
IPC ......... A61N 1/36,1/05, 1/375, 1/04, 1/08; A61F 9/08; A61B 2562/0209, 2562/046, 5/00; G06F 3/011, 3/3406, 19/36
See application file for complete search history.

(56) References Cited

U.S. PATENT DOCUMENTS

| | | |
|---|---|---|
| 4,573,481 A | 3/1986 | Bullara |
| 4,628,933 A | 12/1986 | Michelson |
| 4,837,049 A | 6/1989 | Byers et al. |
| 5,109,844 A | 5/1992 | de Juan, Jr. et al. |
| 5,215,088 A | 6/1993 | Normann et al. |
| 5,649,970 A | 7/1997 | Loeb |
| 5,935,155 A | 8/1999 | Humayun et al. |
| 5,944,747 A | 8/1999 | Greenberg et al. |
| 6,175,767 B1 | 1/2001 | Doyle |
| 6,230,057 B1 * | 5/2001 | Chow et al. ..................... 607/54 |

(Continued)

*Primary Examiner* — Deborah Malamud
(74) *Attorney, Agent, or Firm* — Scott B. Dunbar

(57) ABSTRACT

The present invention is a system for mapping a high resolution image to a lower resolution electrode array and, by applying varying stimulus to neighboring electrodes, creating a perceived image greater in resolution than the electrode array. The invention is applicable to a wide range of neural stimulation devices including artificial vision and artificial hearing. By applying a sub-threshold stimulus to two neighboring electrodes where the sum of the stimuli is above the threshold of perception, a perception is created in neural tissue between the two electrodes. By adjusting the stimulus on neighboring electrodes, the location of stimulation can be altered. Further, noise can be applied to the stimulating electrode or its neighboring electrodes to reduce the threshold of stimulation.

8 Claims, 1 Drawing Sheet

(56) References Cited

U.S. PATENT DOCUMENTS

| | | |
|---|---|---|
| 6,298,270 B1 | 10/2001 | Nisch et al. |
| 6,355,064 B1 | 3/2002 | Peeters et al. |
| 6,400,989 B1 | 6/2002 | Eckmiller |
| 6,458,157 B1 | 10/2002 | Suaning |
| 2002/0010496 A1 | 1/2002 | Greenberg et al. |
| 2002/0037061 A1 | 3/2002 | Learned |

\* cited by examiner

FIELD FOCUSING AND MAPPING IN A VISUAL PROSTHESIS

CROSS REFERENCE TO RELATED APPLICATIONS

This application is a divisional application of U.S. patent application Ser. No. 12/487,498, filed Jun. 18, 2009, for Field Focusing and Mapping in a Visual Prosthesis, which is a divisional application of U.S. patent application Ser. No. 10/355,793, filed Jan. 31, 2003, for Field Focusing and Mapping in an Electrode Array.

FIELD OF THE INVENTION

The present invention is generally directed to electrode arrays, and more particularly to implantable electrode arrays for medical devices.

BACKGROUND OF THE INVENTION

Arrays of electrodes for neural stimulation are commonly used for a variety of purposes. Some examples include: U.S. Pat. No. 3,699,970 to Brindley and "The Sensations Produced by Electrical Stimulation of the Visual Cortex" by G. Brindley and W. Lewin, J. Physiol (London) 196:479-493:1968. Brindley's paper and patent describe an array of cortical electrodes for visual stimulation. One cortical electrode is used for each light percept. Each electrode is attached to a separate inductive coil for signal and power. U.S. Pat. No. 4,573,481 to Bullara describes a helical electrode to be wrapped around an individual nerve fiber. U.S. Pat. No. 4,628,933 to Michelson describes an electrode array for retinal stimulation. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

In addition to the electrode arrays described above, there are several methods of mapping a high resolution camera image to a lower resolution electrode array. U.S. Pat. No. 6,400,989 to Eckmiller describes spatio-temporal filters for controlling patterns of stimulation in an array of electrodes. The assignee of the present applications has three related U.S. patent application Ser. No. 09/515,373, filed Feb. 29, 2000, entitled Retinal Color Prosthesis for Color Sight Restoration and Ser. No. 09/851,268, filed May 7, 2001, entitled Method, Apparatus and System for Improved Electronic Acuity and Perceived Resolution Using Eye Jitter Like Motion. Both applications are incorporated herein by reference.

The density of neural tissue is far greater than currently available electrodes arrays. Using artificial vision as an example, the human retina has approximately 4,000,000 receptors. Further those receptors are not evenly distributed, but are far denser near the fovea, at the center of the retina. The spacing of receptors near the fovea is approximately 5 .mu.m. The best know technology for producing electrodes capable of stimulating retinal neurons requires 40 .mu.m electrodes with 20 .mu.m spaces. Other neural tissues, such as cortical tissue, is about the same scale as retinal tissue. Other neural tissue, such as that found in the optic nerve is far denser. Obtaining a high resolution image is simple and inexpensive using charge coupled device (CCD) cameras. While the mapping systems described above help present the most relevant data given the limited resolution of the electrode array, they do not increase the perceived resolution for the user of a visual prosthesis. A method is needed to direct a high resolution image to a lower resolution electrode array while achieving the highest possible perceived resolution to the individual stimulated by the electrode array.

It is further advantageous to reduce the power needed to stimulate a neuron. As stated above, the smallest possible electrode spacing with current technology is 40 .mu.m electrodes with 20 .mu.m spaces. This assumes a minimal charge requirement. The charge needed varies from retinal to retina, varies across the surface of the retina, and varies over time as retinal disease progresses. Charge density is the charge transferred by an electrode, divided by the surface area of the electrode. As charge density increases, electrochemical reactions at the electrode surface become more intense leading to dissolution of the electrode. It is therefore, advantageous to stimulate neurons with the minimum charge necessary.

SUMMARY OF THE INVENTION

The present invention is a system for mapping a high resolution image to a lower resolution electrode array and, by applying varying stimulus to neighboring electrodes, creating a perceived image greater in resolution than the electrode array. The invention is applicable to a wide range of neural stimulation devices including artificial vision and artificial hearing. By applying a sub-threshold stimulus to two neighboring electrodes where the sum of the stimuli is above the threshold of perception, a perception is created in neural tissue between the two electrodes. By adjusting the stimulus on neighboring electrodes, the location of stimulation can be altered. Further, noise can be applied to the stimulating electrode or its neighboring electrodes to reduce the threshold of stimulation.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
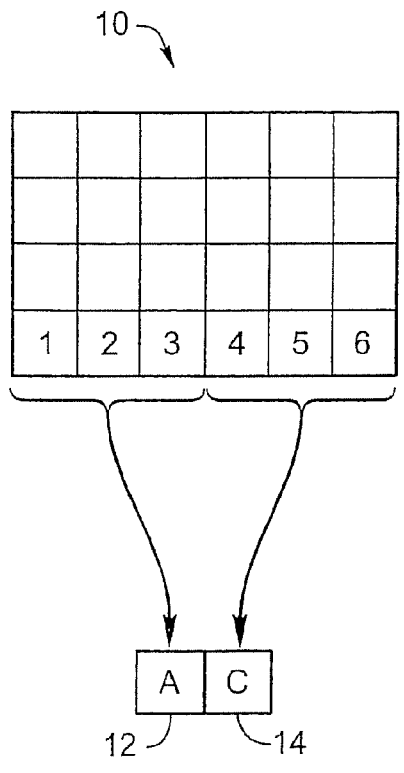
FIG. 1 depicts the prior art method of mapping electrodes.

FIG. 1 shows the prior art. Using a visual prosthesis as an example, a 6 by 4 array of image pixels 10 is mapped to two electrodes, electrode A 12 and electrode C 14 which may be placed on the retinal surface or placed within the visual cortex. The left 12 pixels (columns 1-3) are mapped to electrode A 12 and the right 12 pixels (columns 4-6) are mapped to electrode C 14. The most common mapping is simply taking an average of the twelve pixels. Various modifications to a simple average are known which highlight edges, increase contrast, or otherwise make the limited information more relevant.

All neurons have a threshold potential that causes that neuron to "fire" and send a signal along its neural pathway. It is believed that the firing is caused by creating a capacitive field around the neuron. Although the exact mechanism is not well understood, applying an electrical current at a certain level (super-threshold) will cause the neuron to fire. Current below that level (sub-threshold), will have no effect on the neuron. Applicant has determined through experimental use that applying a sub-threshold electrical current to two adjacent electrodes, where the sum of the signals applied to the two electrodes is super-threshold, will cause a neuron to fire between the two adjacent electrodes. The location between the electrodes is dependent on relative current. A higher current will steer the location of stimulation toward the electrode with the higher current. For simplicity, the effect is described in a single dimension, but works in two dimensions, such as on the retinal surface, or in three dimensions, such as in cortical tissue.

Figure 2:
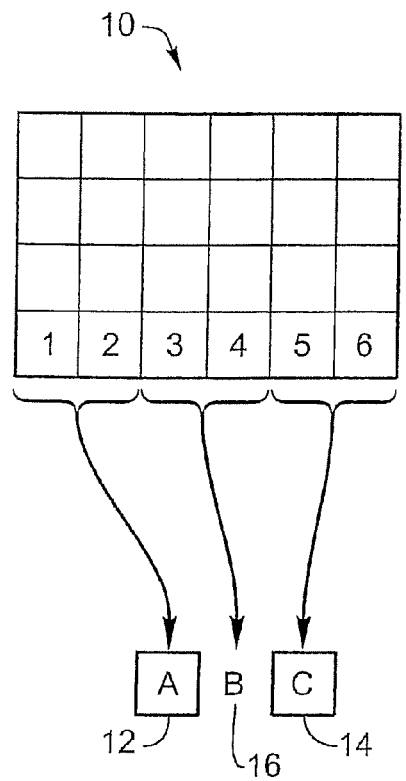
FIG. 2 depicts mapping electrodes according to the present invention.

By using this effect, it is possible to remap image pixels in the visual prosthesis described above to utilize the neurons between electrodes as shown in FIG. 2. The left 8 pixels (columns 1 and 2) are mapped to electrode A 12, the right 8 pixels (columns 5 and 6) are mapped to electrode C 14, and the center 8 pixels (columns 3 and 4) are mapped to the space B 16 between electrode A12 and electrode C 14.

It is possible to enhance this effect, reduce power consumption and reduce the chance of damage to neural tissue, by balancing the currents applied on adjacent electrodes. As an example, if the threshold for neural stimulation is 1 .mu.A (micro amp), and 0.5 .mu.A is applied to electrode A 12 and −0.5 .mu.A is applied to electrode B 14, then one or more neurons will fire causing the perception of a pixel a point B 16, halfway between electrode A 12 and electrode C 14. Applying a charge of 0.8 .mu.A to electrode A 12 and −0.2 .mu.A to electrode C 14 will steer the point of perception toward electrode A 12.

It is possible to obtain multiple point stimulations by rapidly changing the stimulation. Just as we perceived the individual frames of movie as fluid motion, we perceive rapid repeated stimulation as a single image. An example is shown if FIG. 3.

Figure 3:
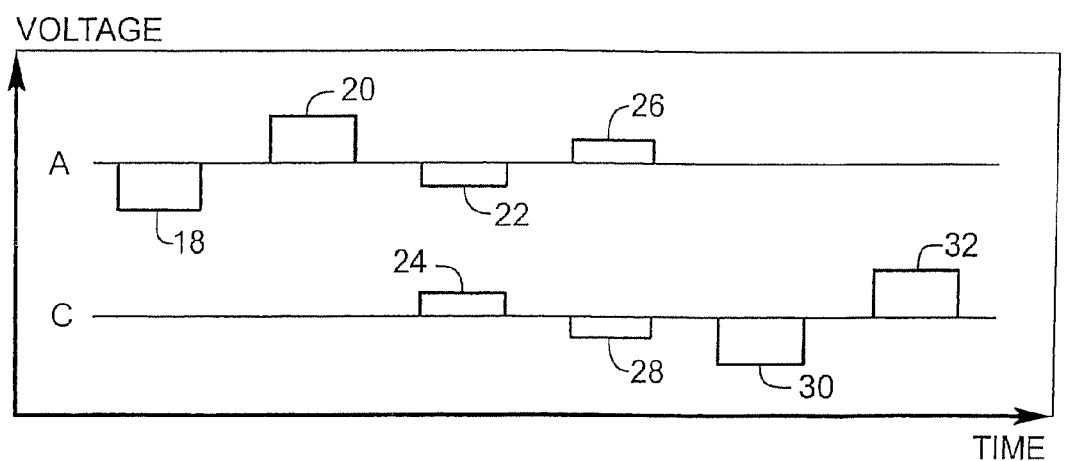
FIG. 3 is a voltage over time plot of stimulating pulses according to the present invention.

FIG. 3 shows the charge applied to electrodes A 12 and C 14 over a typical display cycle. Pulse 18 applied to electrode A 12 is the average of pixels in column 1 and 2. Pulse 20 is equal and opposite to balance the charge. Pulse 22 is one half of the average of the pixels in columns 3 and 4. Pulse 24, applied to electrode C 14 is equal and opposite to pulse 22 (the other half of the average of the pixels in columns 3 and 4). Since it is helpful to balance the charge on each individual electrode, pulse 26 is equal and opposite to pulse 22, and pulse 28 is equal and opposite to pulse 24. Finally, pulse 30, applied to electrode C 14 is equal to the average of the pixels in columns 5 and 6. Pulse 32 is equal and opposite to pulse 30. The decay period in the human visual system is about {fraction (1/50)} of a second. Hence movies displayed at 60 frames per second look fluid while older movies displayed at 30 frames per second appear to flicker. Hence the time line shown in FIG. 3 must be shorter than {fraction (1/50)} of a second to achieve the perception of a continuous image. While FIG. 3 shows stimulation of a single point halfway between electrode A 12 and electrode C 14, it should be understood that the process can be repeated to multiple times to stimulate multiple locations between electrode A 12 and electrode C14.

Applying a noise signal rather than a straight DC charge can reduce the threshold of perception and further improve the process. The noise signal can be applied to the stimulating electrode where a percept is applied directly at the electrode or on neighboring electrodes. Noise stimulation should be sub-threshold and can be immediately before stimulation of a percept or, when on a neighboring electrode, simultaneously with stimulation of a percept.

Accordingly, what has been shown is an improved method of stimulating neural tissue for increased resolution. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A visual prosthesis comprising:
a camera for receiving a pixelized image;
a plurality of electrodes suitable for contact with neural tissue; and
an image processing circuit configured to receive said pixelized image from said camera and configured to map said image to said plurality of electrodes, wherein a set of at least three not linearly placed electrodes are stimulated at a first set of levels to create a percept at a first location between said at least not linearly placed electrodes, and said set of at least three not linearly placed electrodes are stimulated at a second set of levels to create a percept at a second location between said at least not linearly placed electrodes, different from said first location;
wherein said first set of levels and said second set of levels are determined based on mapping said first location and second location from different pixels in said pixelized image.

2. The visual prosthesis according to claim 1, wherein said first set of levels are equal levels on each of said at least three non-linear electrodes.

3. The visual prosthesis according to claim 1, wherein said at least three non-linear electrodes have the same polarity.

4. The visual prosthesis according to claim 1, wherein said at least three non-linear electrodes stimulate with balanced biphasic pulses.

5. The visual prosthesis according to claim 1, wherein pixels from said pixelized image are mapped to said at least three non-linear electrodes as multiple signals in rapid succession such that they form the perception of a single image.

6. The visual prosthesis according to claim 1, wherein some pixels are mapped to said plurality of electrodes wherein a signal from an individual of said plurality of electrodes is insufficient to create the perception of light, but the sum of signals from said plurality of electrodes is sufficient to create the perception of light.

7. The visual prosthesis according to claim 1, wherein varying signals from said at least two electrodes create the perception of light at varying locations between said at least two electrodes.

8. The visual prosthesis according to claim 1, wherein said multiple signals are repeated within one fiftieth of a second.

* * * * *